(12) United States Patent
Li et al.

(10) Patent No.: US 7,608,402 B2
(45) Date of Patent: Oct. 27, 2009

(54) DNA METHYLATION SPECIFIC SIGNAL AMPLIFICATION

(76) Inventors: Weiwei Li, 338 38th St., Lindenhurst, NY (US) 11757; Jessica Li, 338 38th St., Lindenhurst, NY (US) 11757

( * ) Notice: Subject to any disclaimer, the term of this patent is extended or adjusted under 35 U.S.C. 154(b) by 0 days.

(21) Appl. No.: 12/008,292

(22) Filed: Jan. 10, 2008

(65) Prior Publication Data
US 2009/0181373 A1    Jul. 16, 2009

(51) Int. Cl.
*C12Q 1/68* (2006.01)
(52) U.S. Cl. ....................................................... 435/6
(58) Field of Classification Search .................. None
See application file for complete search history.

(56) References Cited
U.S. PATENT DOCUMENTS 5,656,731 A * 8/1997 Urdea ..................... 530/391.1
2002/0127561 A1* 9/2002 Bee et al. ....................... 435/6
2003/0162198 A1* 8/2003 Rothschild et al. ............. 435/6

FOREIGN PATENT DOCUMENTS
WO        WO 02101353 A2 * 12/2002

OTHER PUBLICATIONS

Kang et al., "Highly Sensitive, Specific Detection of O6-Methylguanine, O4-Methylthymine, and O4-Ethylthymine by the Combination of High-Performance Liquid Chromatography Prefractionation, 32P Postlabeling, and Immunoprecipitation," Cancer Research, Oct. 1992, vol. 52, pp. 5307-5312.*
Needels et al., "Generation and screening of an oligonucleotide-encoded synthetic peptide library," PNAS, USA, Nov. 1993, vol. 90, pp. 10700-10704.*
Sano et al., "Detection of heavy methylation in human repetitive DNA subsets by a monoclonal antibody againse 5- methylcytosine," Biochimica et Biophysica, Acta, 1988, vol. 951, pp. 157-165.*

* cited by examiner

Primary Examiner—Young J Kim

(57) ABSTRACT

This invention is related to a method for rapidly detecting gene specific methylation through signal amplification using the epi-barcode after hybrid capture of the methylated DNA sequence.

7 Claims, 5 Drawing Sheets

DNA METHYLATION SPECIFIC SIGNAL AMPLIFICATION

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

1. Field of the Invention

This invention is related to a method for rapidly detecting gene specific methylation through signal amplification using the epi-barcode after hybrid capture of the methylated DNA sequence.

2. Description of the Related Art

DNA methylation is an epigenetic modification which is catalyzed by DNA cytosine-5-methyltransferases (DNMTs) and occurs at the 5-position (C5) of the cytosine ring, within CpG dinucleotides. DNA methylation is essential in regulating gene expression in nearly all biological processes including development, growth, and differentiation (Laird P W et al: Annu. Rev. Genet. 30, 1996; Reik W et al: Science, 293, 2001). Alterations in DNA methylation have been demonstrated to cause a change in the gene expression. For example, hypermethylation leads to gene silencing or the decreased gene expression while hypomethylation activates the genes or increases gene expression. Aberrant DNA methylation is also associated with pathogenesis of diseases such as cancer, autoimmune disorders, and schizophrenia (Baylin S B et al: Nature Clin Pract Oncol Suppl 1, 2005. Richardson B et al: Clin Immunol, 109, 2003. Grayson D R et al: Proc Natl Acad Sci USA, 102, 2005). Most of the current evidences showed that at least in cancer, aberrant DNA methylation could serve a similar function to genetic abnormalities such as inactivating mutations or deletions that lead to abnormal silencing of normal tumor suppressor functions (Garinis G A et al: Hum Genet, 111, 2002). Thus gene/region-specific analysis of DNA methylation could provide valuable information for discovering epigenetic markers used for disease diagnosis, and potential targets used for therapeutics. Furthermore, the methods based on the DNA methylation detection would be highly potential to become disease diagnostic tools.

Many methods for the gene/sequence-specific detection of DNA methylation have been developed over the past decade. Most of these methods are involved in bisulfite conversion of DNA followed by PCR since bisulfite conversion of DNA distinguishes methylated from unmethylated cytosines and enables amplification of DNA methylation to be more specific and reliable. These methods include well-established methylation-specific PCR (MS-PCR), bisulfite sequencing, combined bisulfite restriction analysis (COBRA), and oligonucleotide based microarray (Herman J G et al: Proc Natl Acad Sci USA, 93, 1996; Xiong Z et al: Nucleic Acids Res, 25, 1997; Schumacher A et al: Nucleic Acids Res, 34, 2006). Recently, technically improved methods which are based on the above well-established methods have also been developed. These improved assays enable the detection of DNA methylation to be more specific and quantitative. These assays include real-time methylation-specific PCR such as MethyLight, MethylQuant and QAMA; enzymatic regional methylation assay (ERMA), methylation-specific single-nucleotide primer extension (MS-SNuPE); quantitative bisulfite sequencing using the pyrosequencing technology; and methylation-specific multiplex ligation-dependent probe amplification (MS-MLPA) (Eads C A et al: Nucleic Acids Res, 28, 2000; Thomassin H et al: 32, 2004; Zhang Z et al: Anal Chem, 76, 2004; Gonzalgo M L et al: Nucleic Acids Res, 25, 1997; Collella S et al: Biotechnes, 35, 2003; Nygren A O et al: Nucleic Acids Res, 33, 2005). However most of these methods are labor intensive, time-consuming, and/or require large amounts of DNA (>250 ng) as the starting material for DNA modification and amplification. Additionally, as target amplification methods, they need enzymes in the amplification reaction which often results in inhibition of the amplification reaction due to the reduction or loss of enzymes caused by the sample, reaction components or contaminants. They also require the strict reaction conditions which include preparation of highly pure nucleic acid, the complicated design of primer and probe and use of routinely unavailable equipment. Furthermore, they require liquid phase reaction process which in general, can not enable these methods to be configured for solid phase format such as microarray requiring the generation of localized signals at specific locations. The methylation microarray provides an approach for the massively parallel detection of DNA methylation markers. However reliability of this method is severely limited by the complicated sample preparation process before microarray analysis. This off-chip process involves methylation-sensitive enzyme digestion of DNA or immunoprecipitation of methylated DNA, preamplification of the methylated DNA by PCR and sample labeling, which are time consuming and result in poor reproducibility or low accuracy for the assay. Furthermore, the large amount of DNA for an assay is also required by this method.

Because of these shortcomings, the existing technologies for the detection and quantification of the gene-specific methylation are still not satisfying for the routine application in the biomedical field such as disease diagnosis, food and drug industry monitoring, and environmental monitoring. Thus, there is a need for developing a method to improve the detection and quantification of the gene-specific methylation patterns.

BRIEF SUMMARY OF THE INVENTION

The present invention provides a method for rapidly detecting the methylated DNA sequence. It involves epi-barcode mediated signal amplification of methylated DNA sequence after hybrid capture of the methylated DNA sequence.

The method of the invention has the following advantages over the existing methods:

1. It generates signal amplification of the methylated DNA sequence in a simple manner through the epi-barcode, thus it avoids the enzyme-related contaminations or reaction inhibition often generated by the target amplification methods, while it keeps the powerful amplification ability comparable to the target amplification methods such as PCR.

2. The signal amplification generated by the method of this invention is flexible and controllable. Amplification intensity can range from 10 fold to $1 \times 10^7$ fold or greater, depending on the requirement.

3. It is able to process the amplification reaction in a solid phase format that is suitable for integrating into microarray or biochip platform for high throughput analysis of gene-specific methylation patterns.

DETAILED DESCRIPTION OF THE INVENTION

Figure 1:
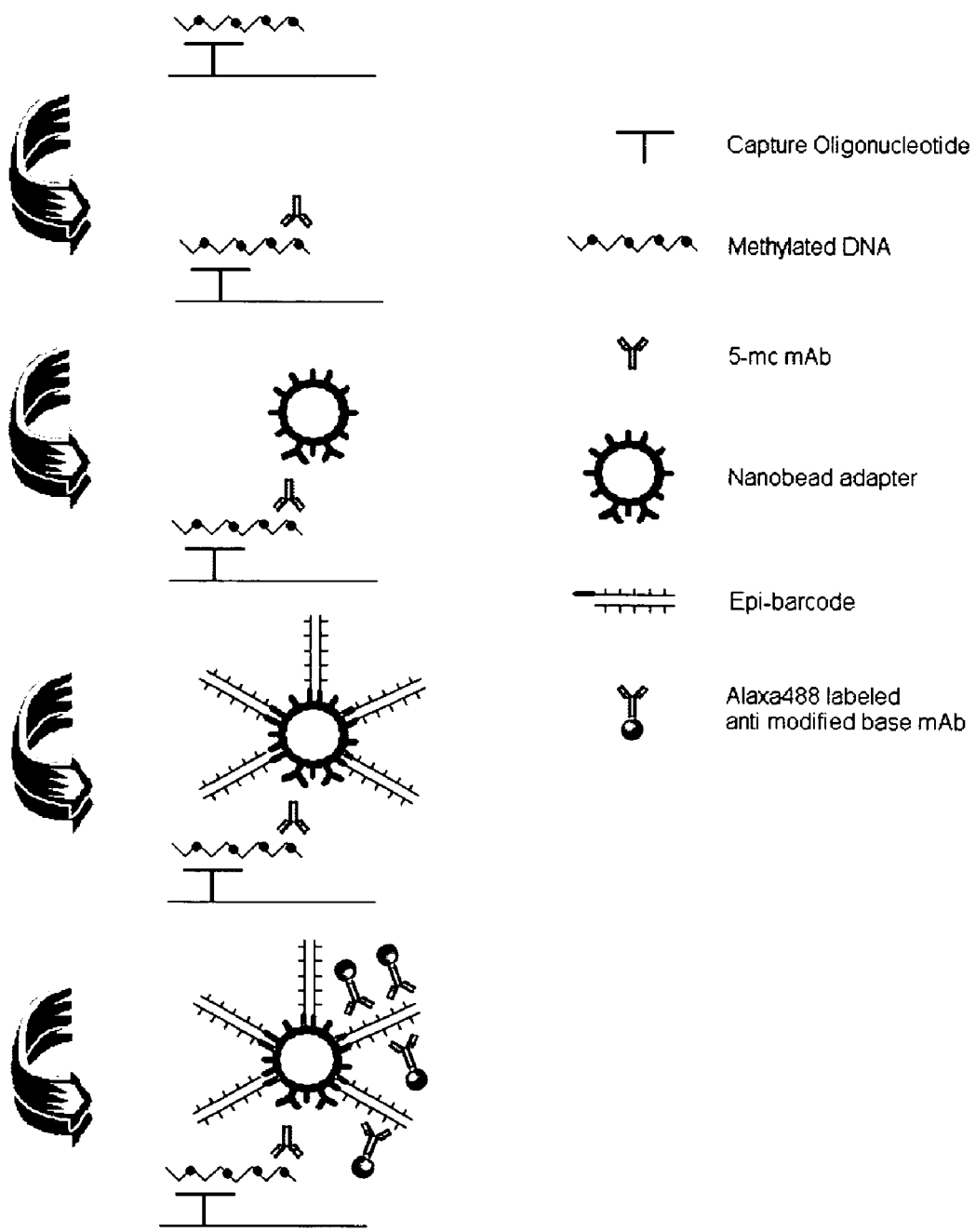
FIG. 1 shows a diagram of epi-barcode based signal amplification process of gene specific methylation. The process involves the following steps: (1) immobilization of capture oligonucleotide on the surface of a solid phase; (2) hybridization of a native or bisulfite-treated DNA fragment containing the target sequence complementary to the capture oligonucleotide; (3) binding of anti-5-methylcytosine antibody to the DNA fragment captured by the capture oligonucleotide; (4) binding of nanobead adaptor to anti-5-methylcytosine antibody bound to the DNA fragment; (5) binding of the epi-barcode to nanobead adaptor; (6) detection of the modified bases contained in epi-barcode with the labeled antibody specific for the modified bases, and optionally, detection of anti-modified base antibody with the secondary antibody conjugated with fluorescent or colorimetric molecules.

The present invention provides a novel method for detecting gene-specific methylation through signal amplification of the methylated DNA sequence. Amplification system based on the method of this invention involves methylation signal conversion on the nanobead adaptor and magnification with the epi-barcode after hybrid capture of the methylated DNA sequence. A basic outline of the method presented in this invention is described in FIG. 1. The method of this invention, with its high amplification ability and specificity, is particularly useful for analyzing gene-specific methylation patterns from a minute amount of a sample with the controlled and consistent (standardizable) results. The method of this invention, with its simplicity and cost-effectiveness, is also particularly useful for routine application in detection or analysis of gene-specific methylation patterns at clinical level.

According to the method of this invention, the single stranded oligonucleotides can be prepared by any conventional oligonucleotide preparation methods such as chemical synthesis and are immobilized as a capture oligonucleotide on a surface of solid phase such as tubes, microtiter plates, multi-well strips, films, beads, particles, papers, membranes and slides. The materials of solid phase include plastic, glass, metals, ceramics, polymers and so forth. The length of the single stranded oligonucleotides is 10-100 nucleotides, preferably 40-50 nucleotides with a sequence complementary to an unmodified DNA sequence containing at least 1 CpG site or with a sequence complementary to a bisulfite modified DNA sequence containing at least 1 CpG site. The surface of solid phase is pre-coated with the substrate containing a reactive group. The oligonucleotides can be modified with a functional group that enables the oligonucleotides to covalently attach to a reactive group on the surface. For example, aminated oligonucleotides can be immobilized onto N-oxysuccinimide-coated glass slides (U.S. Pat. No. 6,391,655). Disulfide-modified oligonucleotides can be immobilized onto a mercaptosilanised glass surface by a thiol/disulfide exchange reaction (Rogers, Y H et al, Anal Biochem, 266: 23, 1999). Immobilization of oligonucleotides can also be achieved by physical absorption on poly-L-lysine, nitrocellulose, nylon membrane and polyacrylamide gels. The appropriate buffer and temperature are required for immobilizing such oligonucleotides on solid phase by either chemical bonding or physical absorption.

According to the method of this invention, the DNA can be isolated by lysis of cells with lysis buffer containing a sodium salt, Tris-HCl, EDTA, and detergents. Tissue fragments should be homogenized before lysing. For example, disaggregation of tissue fragments can be performed by stroking 10-50 times, depending on tissue type, with a Dounce homogenizer. DNA can be further purified by mixing with appropriate buffer and then adding into a column pre-inserted with a silica gel, a silica membrane, or a silica filter. The DNA that binds to the silica matrix is washed by adding a washing buffer and eluted with water. DNA can also be isolated and purified by using commercially available DNA extraction kits such as QiaAmp blood or tissue kits. The starting materials for DNA extraction can be from various biological samples in a form of fresh tissues, frozen tissues, formalin fixed and paraffin embedded tissues, body fluids, and cultured cells.

DNA can be mechanically sheared, chemically sheared or enzymatically digested to yield an appropriate length of the DNA fragment. Usually, 200-500 bp of the sheared or digested DNA is required for hybridization with capture oligonucleotides immobilized on a solid phase. Mechanical shearing of DNA can be performed by nebulization or sonication, preferably sonication. Chemical shearing can be performed by heating, acid catalytic hydrolysis, alkaline catalytic hydrolysis, hydrolysis by metal ions, or hydroxyl radicals. Enzymatic digestion of DNA can be performed by using variety of restriction enzymes, preferably by using DNAse I to facilitate the subsequent hybridization step.

In a further aspect, DNA may be directly modified by standard bisulfite methods or kits commercially available before hybridization to the capture oligonucleotide. More preferably, DNA is modified by a DNA modification method described in prior art (patent application No. 20072042384). This method is particularly useful for gaining a high yield of the modified DNA fragments in a 1-1.5 kb size from a small quantity of starting materials. This method is also particularly useful for modification of DNA in a short time (1-1.5 h).

The sheared or bisulfite-treated DNA fragments are denatured by heating at 95-99° C. for an appropriate time and then hybridized to the capture oligonucleotides immobilized on the surface of the solid phase. The sequence of the capture oligonucleotides is complementary to a portion of the nucleotide sequence of a target DNA fragment. The quick hybridization (0.5-1 h) can be achieved through increasing the hybridization temperature and/or salt concentration of hybridization solution. After capture of target DNA sequence, the hybridization solution is removed and the surface of the solid support is washed. A polyclonal or monoclonal antibody specific for 5-methylcytosine, as a capture antibody, is added to bind to 5-methylcytosine contained in the native or bisulfite-treated DNA fragments. After incubation and washing, the nanobead adaptor solution is added at an appropriate concentration and binds to anti-5-methylcytosine antibody.

A nanobead adaptor is consisted of a carrier bead, a bridge antibody or ligand specifically against the capture antibody, and the holder oligonucleotides. The carrier bead includes but is not limited to polypropylene bead, polystyrene bead, glass bead, metal bead, silica bead, latex bead, and magnetic bead. The bead size may be from 10 nanometers to 900 nanometers in diameter, preferably, from 20 nanometers to 500 nanometers, more preferably from 30 nanometers to 200 micrometers, most preferably from 100 nanometers to 200 nanometers. Most carrier beads are available commercially such as Adembead from Ademtech. The holder oligonucleotide can be selected from the oligo dT, oligo dG, oligo dC and oligo dA, preferably Oligo dT. The length of a holder oligonucleotide should be from 10 to 100 nts, preferably from 15 to 50 nts, most preferably from 20-30 nts.

The preparation of nanobead adaptor can be accomplished through immobilizing bridge antibody or ligand and holder oligonucleotides to the carrier bead. For example, the bridge antibody or ligand and the holder oligonucleotide (after amino modification) can be simultaneously coupled to a carboxylic acid bead. Also, the antibody or ligand and holder oligonucleotides can be first labeled with biotin and then coupled to a streptavidin-coated bead. An appropriate ratio of immobilized bridge antibody or ligand to bridge oligonucleotides can be from 1:100 to 1:10,000, preferably 1:1000. The number of the immobilized holder oligonucleotides is dependent on the size of the carrier bead. A 17 nm nanogold bead can bind approximate 100 holder oligonucleotides. A 200 nm polystyrene bead is able to allow approximate 40,000 holder oligonucleotides to be immobilized.

After binding of nanobead adaptor to capture antibody, the surface of the solid phase is washed again, a solution containing the epi-barcode is then added to bind to the nanobead adaptor. The epi-barcode can be annealed to the holder oligonucleotides through 3'-end complementary poly dA, or poly dT, or poly dC, or poly dG. Each nanobead adaptor could capture 10-1,000 epi-barcodes, depending on its size, and each epi-barcode can have 1-10,000 modified bases, depending on the length of the epi-barcode and number of the modified bases incorporated into the probes.

The epi-barcode consists of the polynucleotides containing modified bases. The polynucleotide can be homopolynucleotide or heteropolynucleotide in a single stranded or double stranded form. The homopolynucleotide includes but is not limited to poly adenosine (poly A), poly cytosine (poly C), poly guanosine (poly G), poly thymidine (poly T), poly uracil (poly U), poly deoxyadenosine (poly dA), poly deoxycytosine (poly dC), poly deoxyguanine (poly dG), poly deoxythymidine (poly dT), poly deoxyuracil (poly dU), poly (dC-dG)•((dC-dG), poly (dI-dC)•(dI-dC), poly (dA-dT)•(dA-dT), poly (dU-dG)•(dU-dG), poly (dC-dT)•(dC-dT), poly (dA-dG)•(dA-dG), poly (dC-dA)•(dC-dA), poly (dG-dT)•(dG-dT), poly (rC-dG)•(rC-dG), poly (rC.dG)•(rC.dG), poly (dI-rC)•(dI-rC), poly (rA-dT)•(rA-dT), and poly (dA.rT)•(dA.rT). The heteropolynucleotide includes but is not limited to synthesized polynucleotides, oligonucleotides, genomic DNA fragment, cDNA fragment, PNA fragment, and plasmid DNA. The modified bases include but are not limited to 2-amino adeninedeoxyriboside, 8-bromo adeninedeoxyriboside, 7-deaza adeninedeoxyriboside, etheno adeninedeoxyriboside, N6-methyl adeninedeoxyriboside, 8-oxo adeninedeoxyriboside, amino-C2-deoxythymidine, amino-C6-deoxycytosine, amino-C6-deoxythymidine, 5'-amino-deoxythymidine, arabinosyl cytosine, 2-amino-deoxyadinine, 8-bromo deoxyadinine, 8-bromo deoxycytosine, 8-bromo deoxyguanine, 8-bromo deoxyuridine, 8-bromo deoxythymidine, carboxy-deoxythymidine, 5-(6-aminohexyl)cytosinedeoxyriboside, 5-bromo cytosinedeoxyriboside, 5-bromo uracilriboside, N4-ethyl cytosinedeoxyriboside, 5-fluoro cytosinedeoxyriboside, cytosine-2'-fluororiboside, cytosine-2'-O-methylriboside, 5-methyl cytosine-2'-O-methylriboside, 5-methyl cytosineriboside, 7-deaza deoxyadenine, 7-deaza deoxyguanine, 5'6-dihydro deoxythymidine, 5'6-dihydro deoxyuridine, EDTA-C2-deoxythymidine, N4-ethyl-deoxycytosine, 5-fluoro deoxycytosine, 5-fluoro deoxyuridine, 5-fluoro cytosineriboside, 5-fluoro uracilriboside, 8-bromo guaninedeoxyriboside, 7-deaza guaninedeoxyriboside, iso guaninedeoxyriboside, 8-oxo guaninedeoxyriboside, 6-thio guaninedeoxyriboside, guanine-2'-O-methylriboside, 5-hydroxyl deoxycytosine, 5-hydroxyl deoxyuridine, 5-hydroxymethyl deoxyuridine, 5-nitro indoledeoxyriboside, 06-phenyl indoledeoxyriboside, Inosine-2'-O-methylriboside, 5'-Iodo deoxythymidine, 5'-Iodo uracilriboside, 5-Iodo deoxycytosine, 5-methylcytosine, 5-methyl deoxyadenine, 5-methyl deoxycytosine, 5-methyl deoxycytidine, 5-methyl-iso cytosine, 5-methyl cytosineriboside, 5-methyl uracilriboside, O6-methyl deoxyguanine, O6-methyl-deoxythymidine, 2'-O-methyl-2-amino adenineriboside, 2'-O-methyl-3-deaza-5-aza-cytosineriboside, 2'-O-methyl adenineriboside, 2'-O-methyl cytosineriboside, 2'-O-methyl-5-Br-uridineriboside, 2'-O-methyl-5-fluoro-uridineriboside, 2'-O-methyl-5-methyl-uridineriboside, 2'-O-methyl-5-methyl-cytosineriboside, 2'-O-methylguanineriboside, 2'-O-methyl uridineriboside, 2'-O-methyl thymidine, N6-methyl deoxyadenine, 5-nitroindole, 3-nitropyrrone, 8-oxo-deoxyadenine, 8-oxo-deoxyguanine, 5-OH-deoxycytosine, 5-OH-deoxyuridine, 5-O-methyl deoxythymidine, O6-phenyl deoxyinosine, Tamara-deoxythymidine, 2-thiol deoxythymidine, 6-thiol deoxyguanine, 4-thiol deoxythymidine, 4-thiol deoxyuridine, 4-thiol-uracilriboside, 5-Iodo thyminedeoxyriboside, 5-O-methyl thyminedeoxyriboside, O4-methyl thyminedeoxyriboside, 2-thiol thyminedeoxyriboside, 4-thiol thyminedeoxyriboside, 5-tamra thyminedeoxyriboside, O4-triazolyl thyminedeoxyriboside, 5(3-acrylic) uracildeoxyriboside, 5-(6-aminohexyl)uracildeoxyriboside, 5-bromo uracildeoxyriboside, 5-iodo uracildeoxyriboside, 4-thio uracildeoxyriboside, uridine-2-fluoro-riboside, uridine-2-O-methylriboside, 5-bromo uridine-2-O-methylriboside, 5-fluoro uridine-2-O-methylriboside, and 5-methyl uridine-2-O-methylriboside.

The modified bases can be chemically synthesized and the modified bases-contained homopolynucleotide or heteropolynucleotide can be generated through enzymatic synthesis or PCR-based development of polynucleotide.

According to the method of this invention, an epi-barcode is preferably a homopolynucleotide or heteropolynucleotide with the modified bases of N6-methyl deoxyadenosine, or O6-methyl deoxyguanine, or O6-methyl-deoxythymidine, or 5-methylcytosine, or 5-methyldeoxycytosine, or 5-methylcytidine, or 5-methyldeoxycytidine. More preferably, a poly A or a poly dA or a poly (dA-dT)•(dA-dT), or a plasmid DNA with modified bases of N6-methyl deoxyadenosine, or a poly C or a poly dC or a poly (dI-dC)•(dI-dC) or a poly (dC-dG)•((dC-dG), or a plasmid DNA with modified bases of 5-methylcytosine, or 5-methyldeoxycytosine, or 5-methylcytidine, or 5-methyldeoxycytidine. Most preferably, a poly C or a poly dC or a poly (dI-dC)•(dI-dC) or a poly (dC-dG)•(dC-dG), or a plasmid DNA with modified bases of 5-methylcytosine, or 5-methyldeoxycytosine, or 5-methylcytidine, or 5-methyldeoxycytidine. The length of the polynucleotide can be from 10 to 10000 bases or base pairs in a homopolynucleotide form, or from 20 to 100,000 bases or base pairs in a heteropolynucleotide form. The number of modified bases can be from 1 to 10,000 for the homopolynucleotide and from 1 to 30,000 for the heteropolynucleotide.

The polynucleotide containing the modified bases can be then tailed with poly dA, or poly dT, or poly dC or poly dG to form epi-barcode. According to the method of this invention, the polynucleotide is preferably tailed with poly dA or poly dT, through terminal deoxynucleotidyl transferase-based DNA tailing method. By using this method, mononucleotide from dATP, or dTTP, can be repeatedly added to the terminal 3' hydroxyl of single or double-stranded polynucleotides. The length of the nucleotide tail can be from 1 to 400 nts, preferably from 10 to 100 nts, more preferably from 20 to 50 nts, most preferably 30 nts. According to the method of this invention, a poly dA-tailed poly (dI-dC)·(dI-dC) with modified bases of 5-methylcytosine (poly (dI-MdC)·(dI-MdC)) is used as the epi-barcode. Through such a way, a 900 nm nanobead adaptor can carry up to 1,000 epi-barcodes, or $1 \times 10^7$ modified bases, as each epi-barcode could contain up to 10,000 modified bases.

A polyclonal or monoclonal antibody which recognizes and binds to modified bases can be generated according to various methods described in prior art. The generated antibody can be further conjugated with biotin, or enzymatic label molecules such as HRP and AP, or fluorescent label molecules such as Alaxa fluor, cy3, cy5 and FITC, or gold label molecules, or quantum dot label molecules. Such a conjugated antibody is then applied to bind to the epi-barcode containing the modified bases and the colorimetric or fluorescent signal can be developed and quantified. If the antibody is conjugated with biotin, the enzymatic or fluorescent molecule labeled streptavidin can be used to bind to the biotin labeled antibody specific to the modified bases. The colorimetric or fluorescent development is then carried out. If the unconjugated antibody is chosen for binding to modified bases, a secondary anti-mouse, or anti-rabbit, or anti-goat or anti-sheep antibody conjugated with above label molecules can be used to bind to the unconjugated antibody specific to the modified bases. The colorimetric or fluorescent development is then carried out. The intensity of the signal amplification reactions can be calculated with the following equation: amplification intensity (AI)=M×N. Here, M is the number of modified bases in the epi-barcode; N is the number of the epi-barcode annealed to nanobead adaptor. The signal intensity of the target methylated DNA sequence can be flexibly enhanced from 10 fold to $1 \times 10^7$ fold, depending on the number of modified bases on the epi-barcode, the length of epi-barcode and the size of nanobead adaptor.

According to the method of this invention, as low as a single DNA molecule containing only 2-3 methylated CpG sites can be detected through fluorescent measurement. The detection of the gene-specific methylation patterns can be carried out in a single strip well, or a multiple well strip, or a 96-1536 well microplate or a microchip slide. A complete detection or quantification of the gene-specific methylation patterns needs only 4 hours.

The method of this invention is useful in detecting the gene-specific methylation patterns using a biological sample. The method of this invention may be particularly useful in detecting the gene-specific methylation patterns in a clinical sample with a minute amount of DNA. These clinical samples may include but are not limited to tissue biopsy, tissue section, formalin fixed, paraffin embedded (FFPE) specimens, plasma, serum, cerebro-spinal fluid, tears, sweat, lymph fluid, saliva, nasal swab or nasal aspirate, sputum, bronchoalveolar lavage, breast aspirate, pleural effusion, peritoneal fluid, glandular fluid, amniotic fluid, cervical swab or vaginal fluid, ejaculate, semen, prostate fluid, urine, conjunctival fluid, duodenal juice, pancreatic juice, bile and stool. The method of this invention may be more particularly useful in the development of a simple and cost-effective assay for detecting DNA methylation biomarkers of important diseases such as cancer, infectious diseases, heart diseases, and neurodegenerative diseases.

The method of this invention for detecting gene-specific methylation is further illustrated in the following examples:

EXAMPLE 1

The experiment was carried out to test the stability and the efficiency of the nanobead adaptor binding to capture antibody.

1. Preparation of nanobead adaptor. The nanobead size and type are selected based on that the specific binding of the beads to the target should be stable and tight with minimal non-specific background, while the surface area of the beads should be as large as possible for maximally conjugating bridge antibody and holder oligonucleotides. The streptavidin-coated magnetic beads in a diameter of 200 nm were found to be the most appropriate. To prepare the functionalized nanobead adaptor, 1 mg of the beads (approximately $1 \times 10^{10}$ beads) is washed twice with PBS and resuspended in the 1 ml of PBS. 20 µl (10 pg/ml) of biotin-labeled anti-mouse IgG, as bridge antibody and 20 µl (50 pmol/µl) of 5-biotin-labeled oligo (dT)25 as holder oligonucleotides are added into the suspended beads solution, respectively. The mixed solution is incubated at room temperature for 45 min and then wash 4 times with PBS by applying a magnetic field. The bead pellet is then suspended in the 1 ml PBS and stored in 4° C. Through such a way, one bead could conjugate approximate 40 bridge antibody molecules and 40,000 holder oligo (dT) 25.

Figure 2:
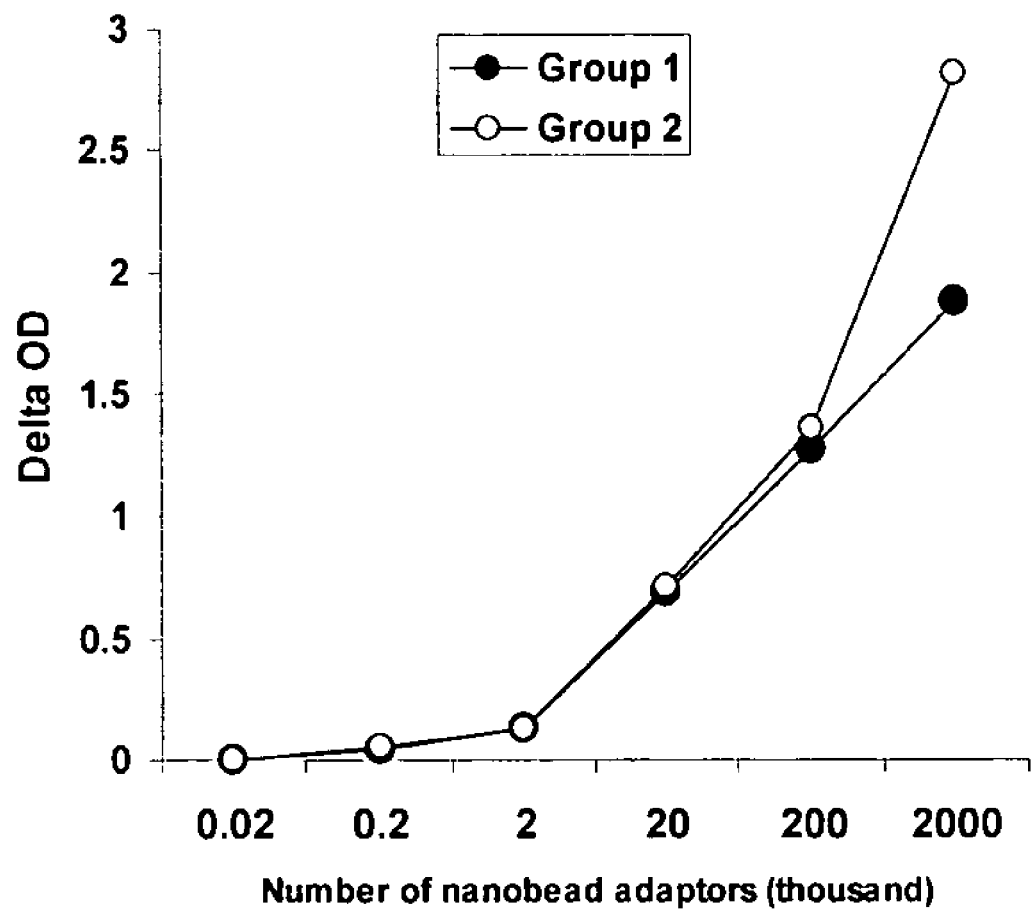
FIG. 2 shows the stability and efficiency of nanobead adaptor bound to the target antibody.
Figure 3:
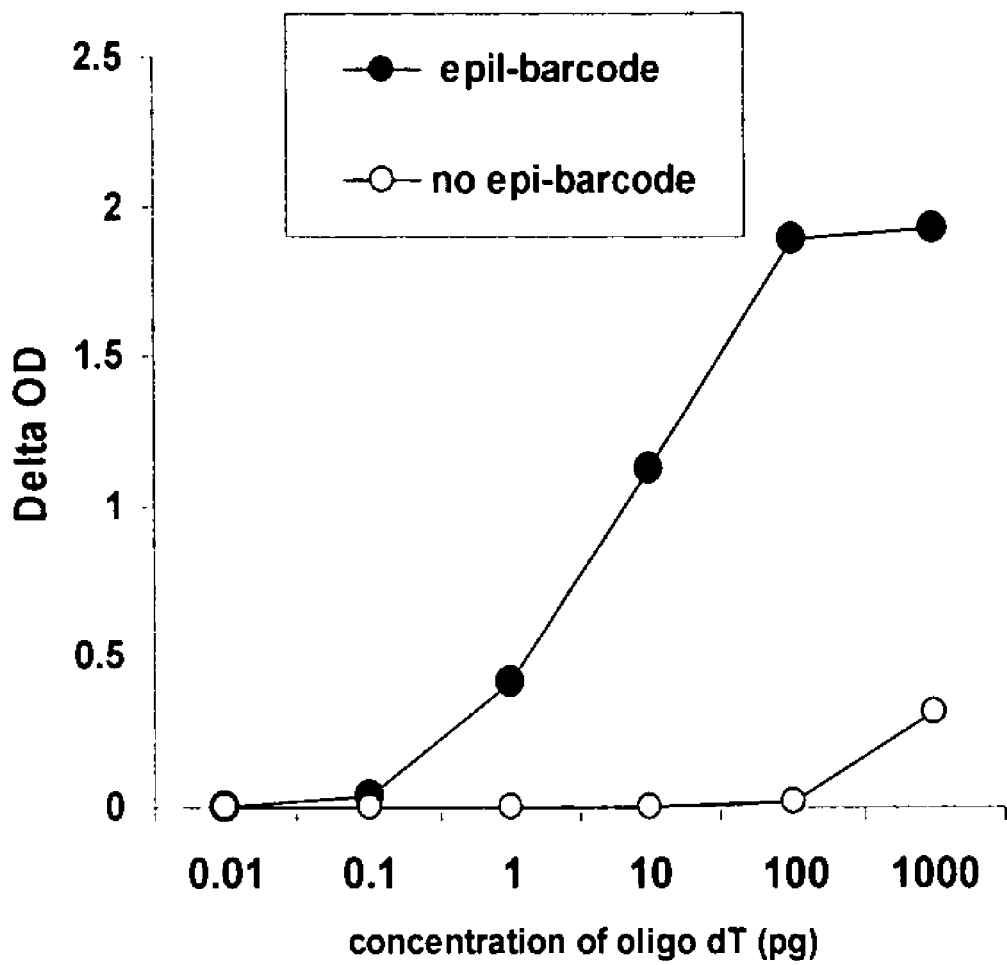
FIG. 3 shows the signal amplification capacity of epi-barcode.

2. Testing the stability and the efficiency of nanobead adaptor binding to capture antibody In group 1, nanobead adaptors were diluted to different concentrations and 100 µl of the diluted nanobead adaptor solutions were added into the 5-MC mAb coated stripwells. The wells were washed with PBS-T for 8 times after 1 h incubation. Anti-biotin antibody-HRP was added and wells were washed with PBS-T for an additional 8 times after 30 min incubation. In group 2, the same amounts of diluted nanobead adaptor solutions were added into the 0.5 ml vials. Anti-biotin antibody-HRP was added into the diluted nanobead adaptor solutions and beads were washed 4 times by applying a magnetic field after 30 min incubation. The color development was carried out for both groups and OD values were measured at 450 nm using a microplate reader. The nanobead adaptor in a diameter of 200 nm was able to stably bind to the target antibody after extensively washing (FIG. 2). Nearly 100% of nanobead adaptors added into wells bound to the target antibody except that at the highest concentration (total bead number excesses the binding capacity of the well).

EXAMPLE 2

The experiment was carried out to test signal amplification capacity of epi-barcode.

1. Preparation of epi-barcode. Poly (dI-dC)·(dI-dC) in a length of 7000 base pairs was treated with the mixed DNA methylases consisted of MSss.I and Dnmt 1 for 16 h. to allow every cytosine contained in Poly (dI-dC)·(dI-dC) to be methylated. The methylated poly (dI-dC)·(dI-dC) or poly (dI-MdC)·(dI-MdC) is then tailed in the 3'-terminal with poly (dA) through using terminal deoxynucleotidyl transferase-based DNA tailing method.

2. Testing signal amplification capacity of epi-barcode. The aminated oligo (dT) 25 in different amounts (0.01 pg-1000 pg) were coupled to the NOS-DNA Bind stripwells.

The poly dA-tailed epi-barcodes were applied to the wells followed by adding 5-MC mAb and then anti-mouse IgG-HRP. Meanwhile, the biotin-labeled oligo (dA) was also added into the wells followed by adding anti-biotin antibody conjugated with HRP. The color development was carried out and OD values were measured. The results showed that signal intensity of a target molecule can be enhanced up to 1000-1500 folds by a single epi-barcode.

EXAMPLE 3

Figure 4:
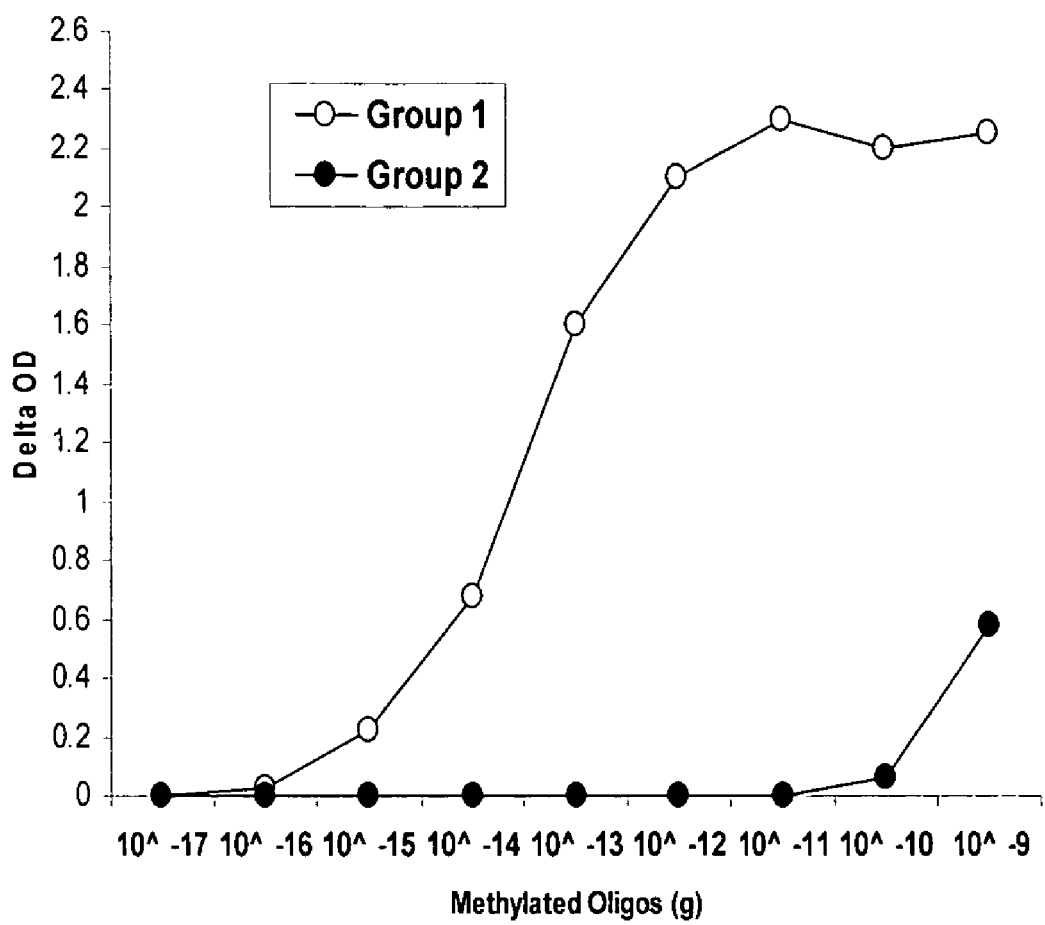
FIG. 4 shows sensitivity of the method of this invention in quantifying the methylated DNA sequences

The experiment was carried out in two groups to detect the sensitivity of the method of this invention in quantifying methylated DNA sequences. In group 1, 5 µM of a 50 mer aminated capture oligonucleotides complementary to the 40 mer methylated oligonucleotides containing 6 methylated CpGs were immobilized on the NOS-DNA Bind microplate wells. The methylated oligonucleotides were diluted to 0.1 fg-10 ng/ml and 100 µl of the methylated oligonucleotides were then hybridized to the 50 mer capture oligonucleotides at 46° C. for 0.5-1 h. After washing with 0.2×SSC containing 0.1% tween-20, 50 µl of mouse monoclonal 5-methylcytidine antibody at 1 pg/ml was added and the wells were incubated at room temperature for 1 h. After washing with PBS-tween 20, 100 µl of nanobead adaptor solution (1,000,000 beads/ml) was added and the wells were incubated at room temperature for 30 min. 50 µl of epi-barcode (400 ng/ml) was then added into the wells after washing with PBS-tween 20 solution and the wells were incubated at room temperature for 30 min. After washing with PBS-tween 20, mouse monoclonal 5-methylcytidine antibody at 1 pg/ml was added again and the wells were incubated at room temperature for 1 h. The wells were washed with PBS-tween 20. 50 µl of anti-mouse antibody conjugated with HRP at 0.5 µg/ml was added into the wells and incubated at room temperature for 30 min. After the wells were washed with PBS-tween 20, the color development solution containing TMB was added into the wells and wells were observed for 2-10 min for blue color appearance. The 1 M HCl or $H_2SO_4$ solution was added to stop the color development and the optical density was measured with a microplate reader. In group 2, the process was same as that in group 1 until mouse monoclonal 5-methylcytidine antibody was added first time and the wells were incubated. After this step, the wells were washed and HRP-conjugated anti-mouse antibody was added into the wells and incubated at room temperature for 30 min. The wells were washed with PBS-tween-20. The color development solution containing TMB was added into the wells and wells were observed for 2-10 min for blue color appearance. The 1 M HCl or $H_2SO4$ solution was added to stop the color development and the optical density was measured with a microplate reader. The result is shown in FIG. 4.

EXAMPLE 4

Figure 5:
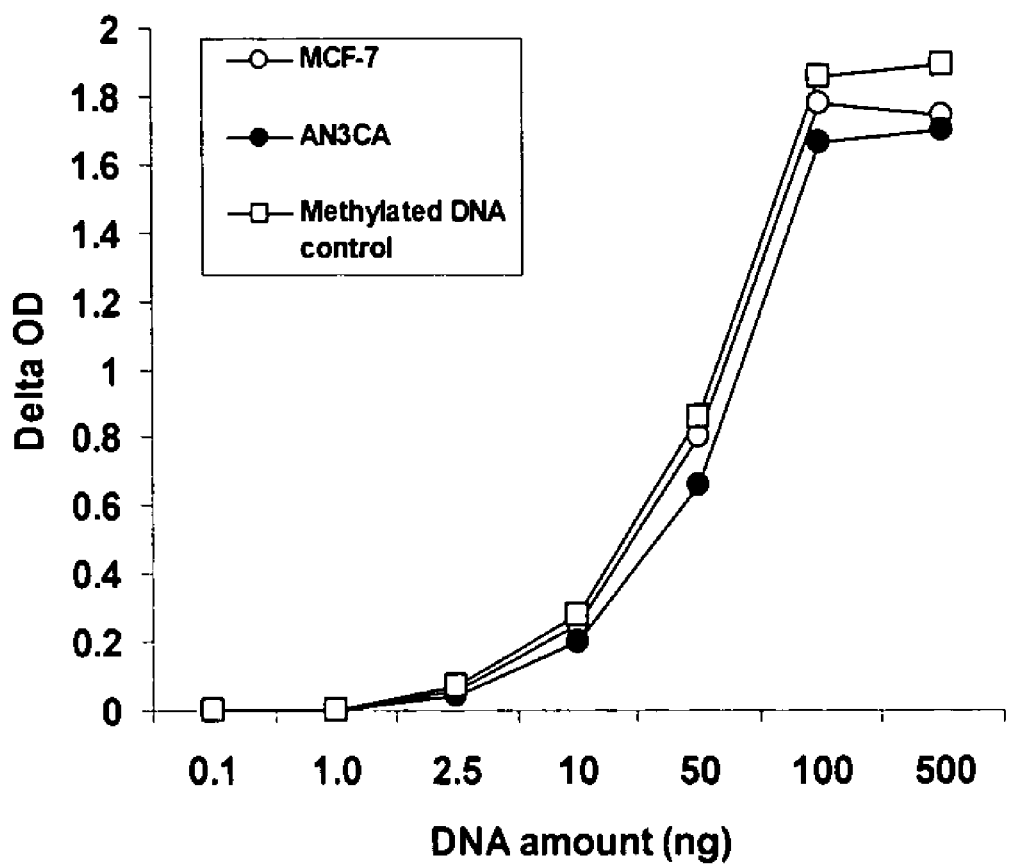
FIG. 5 shows the ability of the method of this invention for detecting gene-specific methylation using cancer cell samples.

The experiment was carried out to test the ability of the method of this invention for detecting gene-specific methylation patterns using different cancer cell samples. 5 µM of a 50 mer aminated capture oligonucleotides, which is complementary to the sequence (18007-18056, access No: AC002481) of the human RASSF1A proximal promoter were immobilized on the NOS-DNA Bind microplate wells. Fully methylated genomic DNA (Chemicon) and DNA isolated from MCF-7 and AN3CA cancer cell lines (ATCC) were fragmented to 200-600 bps by sonication, diluted to 0.1-5000 ng/ml and denatured at 95° C. for 5 min. 100 µl of denatured DNA were then hybridized to the 50 mer capture oligonucleotides at 46° C. for 0.5-1 h. After washing with 0.2×SSC containing 0.1% tween-20, 50 µl of monoclonal 5-methylcytidine antibody at 1 µg/ml was added and the wells were incubated at room temperature for 1 h. After washing with PBS-tween 20, the nanobead adaptor solution (1,000, 000 beads/ml) were added and the wells were incubated at room temperature for 30 min. 50 µl of epi-barcode (400 ng/ml) were then added into the wells after washing with PBS-tween 20 solution and the wells were incubated at room temperature for 30 min. After washing with PBS-tween 20, mouse monoclonal 5-methylcytidine antibody at 1 pg/ml was added again and the wells were incubated at room temperature for 1 h. The wells were washed with PBS-tween 20, 50 µl of anti-mouse antibody conjugated with HRP at 0.5 µg/ml was added into the wells and incubated at room temperature for 30 min. The wells were washed with PBS-tween 20. The color development solution containing TMB was added into the wells and wells were observed for 2-10 min for blue color appearance. The 1 M HCl or $H_2SO4$ solution was added to stop the color development and the optical density was measured with a microplate reader. The result is shown in FIG. 5.

EXAMPLE 5

The experiment was carried out to detect the specificity of the method of this invention in quantifying gene-specific methylation patterns. 5 µM of 50 mer capture oligonucleotides which are complementary to the sequence of human GSTP1 promoter (1862-1910, access No: AY324387) and complementary to the sequence (131-180, access No. U40960) of the MLH1 exon 1, respectively were immobilized on the NOS-DNA Bind microplate wells. Fully methylated human genomic DNA and DNA isolated from MCF-7, AN3CA cancer cells and IMR90 human fibroblast cells (ATCC) were fragmented to 200-600 bps by sonication and denatured at 95° C. for 5 min. 100 µl (100 ng) of denatured DNA were then hybridized to the 50 mer capture oligonucleotides at 46° C. for 0.5-1 h. After hybridization, the epi-barcode based signal amplification reaction was processed as described in the example 4. Meanwhile, a real-time quantitative PCR was carried out as a control to detect methylation-specific amplification reaction of GSTP1 and MLH1 genes. The β-actin gene was used as an internal reference. The primers are specific to methylated DNA of interest. The sequence-specific probes were labeled with either FAM or TET. The probe was quenched with a black hole quencher and conjugated with a minor groove binder (MGB) protein at its 3' portion. 20 µl of PCR mixture was prepared by the addition of the bisulfite-treated DNA (2 ng), Taq enzyme, PCR buffer, a primer sets and a probe. Reactions were carried out with the following temperature settings: 1 cycle of 95° C. for 4 minutes, 50 cycles of 94° C. for 30 seconds, 55° C. for 30 seconds and 72° C. for 30 seconds. The result is shown in the table 1.

TABLE 1

Specificity comparison between the method of this invention and real time PCR in detecting gene-specific methylation

| | Method of this invention (delta OD) | | Real time PCR (CTs) | |
|---|---|---|---|---|
| | GSTP1 | MLH1 | GSTP1 | MLH1 |
| MCF-7 | 1.45 | −0.06 | 31.6 | N/A |
| AN3CA | 0.02 | 1.38 | N/A | 34.6 |
| IMR90 | 0.02 | −0.04 | N/A | N/A |

TABLE 1-continued

Specificity comparison between the method of this invention and real time PCR in detecting gene-specific methylation

| | Method of this invention (delta OD) | | Real time PCR (CTs) | |
|---|---|---|---|---|
| | GSTP1 | MLH1 | GSTP1 | MLH1 |
| Positive control (methylated DNA) | 1.49 | 1.32 | 31.9 | 34.3 |
| H$_2$O | 0 | 0 | N/A | N/A |

What is claimed is:

1. A method for amplifying methylation specific signal generated from methylated DNA sequence in a DNA sample comprising steps of: a) binding of a nanobead adaptor consisted of a carrier bead, a bridge antibody and holder oligonucleotides to anti-5-methylcytosine antibody bound to said methylated DNA sequence; b) binding of an epi-barcode consisting of polynucleotides therefore containing 5-methylcytosine to nanobead adaptor; and c) detection of the presence of the epi-barcode with the anti-5-methylcytosine antibody wherein the amount of the epi-barcode bound to nanobead adaptor determines the amplification intensity of methylation specific signal generated from said methylated DNA sequence in the DNA sample.

2. The method according to claim 1 wherein said carrier bead is a polypropylene bead or a magnetic bead in the size of 5 nm to 900 nm in diameter and coated with streptavidin, avidin or neutravidin.

3. The method according to claim 1 wherein said bridge antibody is anti-mouse, or anti-rabbit, or anti-goat, or anti-sheep, or anti-chicken IgG or IgM and labeled with biotin.

4. The method according to claim 1 wherein said holder oligonucleotides are oligo dT, or oligo dG, or oligo dC, or oligo dA with a length of 10 to 100 nucleotides and labeled with biotin.

5. The method according to claim 1 wherein said nanobead adaptor is formed through immobilizing bridge antibody and holder oligonucleotides to the carrier bead.

6. The method according to claim 1 wherein said epi-barcode is the synthesized poly (dI-dC)•(dI-dC), or poly (dC-dG)•((dC-dG) with a length of 3-10,000 bases or base pairs containing 1-10,000 5-methylcytosines.

7. The method according to claim 1 wherein said epi-barcode is labeled with biotinylated dATP, dCTP, dGTP, dTTP, or dUTP or tailed with poly dA, or poly dT, or poly dC, or poly dG.

* * * * *